United States Patent
Lamps et al.

(10) Patent No.: US 8,398,664 B2
(45) Date of Patent: Mar. 19, 2013

(54) LANCING DEVICE AND LANCET

(75) Inventors: Gregory Lamps, Smyrna, GA (US);
Brian M. Collins, Marietta, GA (US);
Lauren R. Pusey, Woodstock, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 345 days.

(21) Appl. No.: 12/641,684

(22) Filed: Dec. 18, 2009

(65) Prior Publication Data

US 2010/0160943 A1    Jun. 24, 2010

Related U.S. Application Data (60) Provisional application No. 61/138,768, filed on Dec. 18, 2008.

(51) Int. Cl.
*A61B 17/32* (2006.01)

(52) U.S. Cl. ................................. 606/181

(58) Field of Classification Search .......... 606/181–185, 606/172; 600/583, 573, 576, 578; 604/187, 604/208–211, 110
See application file for complete search history.

(56) References Cited

U.S. PATENT DOCUMENTS

| | | | |
|---|---|---|---|
| 4,203,446 A * | 5/1980 | Hofert et al. ............... | 606/182 |
| 4,895,147 A | 1/1990 | Bodicky et al. | |
| 4,924,879 A | 5/1990 | O'Brien | |
| 4,976,724 A | 12/1990 | Nieto et al. | |
| 5,196,025 A * | 3/1993 | Ranalletta et al. ........... | 606/182 |
| D342,573 S | 12/1993 | Cerola | |
| 5,282,822 A | 2/1994 | Macors et al. | |
| 5,318,584 A | 6/1994 | Lange et al. | |
| 5,423,847 A | 6/1995 | Strong et al. | |
| 5,464,418 A | 11/1995 | Schraga | |
| 5,554,166 A | 9/1996 | Lange et al. | |
| 5,613,978 A | 3/1997 | Harding | |
| D379,516 S | 5/1997 | Rutter | |
| 5,730,753 A | 3/1998 | Morita | |
| RE35,803 E | 5/1998 | Lange et al. | |
| 5,916,230 A | 6/1999 | Brenneman et al. | |
| 5,954,738 A | 9/1999 | LeVaughn et al. | |
| 5,984,940 A | 11/1999 | Davis et al. | |
| 6,022,366 A | 2/2000 | Schraga | |
| 6,045,567 A | 4/2000 | Taylor et al. | |
| D428,150 S | 7/2000 | Ruf et al. | |
| 6,156,050 A | 12/2000 | Davis et al. | |

(Continued)

FOREIGN PATENT DOCUMENTS

| EP | 1779781 A2 | 5/2007 |
|---|---|---|
| WO | 0128423 A2 | 4/2001 |

OTHER PUBLICATIONS

Invitation to Pay Additional Fees and Partial Search Report for PCT/US2009/068674; Apr. 8, 2010; 8 pgs.

(Continued)

*Primary Examiner* — Kathleen Holwerda
*Assistant Examiner* — Jocelin Tanner
(74) *Attorney, Agent, or Firm* — Gardner Groff Greenwald & Villanueva, PC (57) ABSTRACT

A lancing device and lancet are provided with depth-control, lancet ejection, and/or guidance mechanisms. The depth-control mechanism includes a dial rotationally mounted at a distal end of the housing of the lancing device, the dial being coupled to a linkage whereby rotation of the dial imparts translational movement to a stop surface of the linkage to limit the stroke of the lancet and thereby control lancing penetration depth. The ejection mechanism includes an ejector that is advanced into contact with a transversely flared flange of the lancet to discharge the lancet from the lancing device. The guidance mechanism includes an inner guidance housing for restricting out-of-axis movement of a lancet carrier.

22 Claims, 9 Drawing Sheets

U.S. PATENT DOCUMENTS

| | | | |
|---|---|---|---|
| 6,156,051 A | 12/2000 | Schraga | |
| 6,168,606 B1 | 1/2001 | Levin et al. | |
| 6,197,040 B1 | 3/2001 | LeVaughn et al. | |
| D444,557 S | 7/2001 | LeVaughn et al. | |
| D447,566 S | 9/2001 | LeVaughn et al. | |
| 6,283,982 B1 | 9/2001 | LeVaughn et al. | |
| 6,322,575 B1 | 11/2001 | Schraga | |
| 6,332,871 B1 | 12/2001 | Douglas et al. | |
| 6,409,740 B1 | 6/2002 | Kuhr et al. | |
| 6,419,661 B1 | 7/2002 | Kuhr et al. | |
| 6,451,040 B1 | 9/2002 | Purcell | |
| 6,514,270 B1 | 2/2003 | Schraga | |
| 6,530,937 B1 | 3/2003 | Schraga | |
| 6,558,402 B1 | 5/2003 | Chelak et al. | |
| 6,575,939 B1 | 6/2003 | Brunel | |
| 6,602,268 B2 | 8/2003 | Kuhr et al. | |
| 6,645,219 B2 | 11/2003 | Roe | |
| 6,749,618 B2 | 6/2004 | LeVaughn et al. | |
| D493,532 S | 7/2004 | LeVaughn et al. | |
| 6,811,557 B2 | 11/2004 | Schraga | |
| 6,887,253 B2 | 5/2005 | Schraga | |
| 6,986,777 B2 | 1/2006 | Kim | |
| 7,105,006 B2 | 9/2006 | Schraga | |
| D530,424 S | 10/2006 | Manser et al. | |
| 7,175,641 B1 | 2/2007 | Schraga | |
| 7,223,276 B2 | 5/2007 | List et al. | |
| 7,273,484 B2 | 9/2007 | Thoes et al. | |
| 7,288,102 B2 | 10/2007 | Griffin et al. | |
| 7,311,718 B2 | 12/2007 | Schraga | |
| D560,805 S | 1/2008 | Young et al. | |
| 7,322,998 B2 | 1/2008 | Kuhr et al. | |
| D581,533 S | 11/2008 | Ruf et al. | |
| D586,465 S | 2/2009 | Faulkner et al. | |
| D586,916 S | 2/2009 | Faulkner et al. | |
| 7,510,564 B2 | 3/2009 | Mace | |
| 7,651,512 B2 | 1/2010 | Chelak et al. | |
| 7,655,019 B2 | 2/2010 | LeVaughn et al. | |
| D612,051 S | 3/2010 | Ruf | |
| 7,678,126 B2 | 3/2010 | Schraga | |
| 7,678,127 B2 | 3/2010 | Trissel et al. | |
| 7,682,318 B2 | 3/2010 | Alden et al. | |
| 2003/0028126 A1* | 2/2003 | List | 600/583 |
| 2003/0088261 A1 | 5/2003 | Schraga | |
| 2003/0212344 A1 | 11/2003 | Yuzhakov et al. | |
| 2004/0039302 A1 | 2/2004 | Kim | |
| 2004/0162573 A1 | 8/2004 | Kheiri | |
| 2004/0236362 A1* | 11/2004 | Shraga | 606/181 |
| 2005/0125017 A1 | 6/2005 | Kudrna et al. | |
| 2005/0125019 A1 | 6/2005 | Kudrna et al. | |
| 2005/0159768 A1 | 7/2005 | Boehm et al. | |
| 2005/0234492 A1 | 10/2005 | Tsai et al. | |
| 2005/0234495 A1 | 10/2005 | Schraga | |
| 2005/0288699 A1* | 12/2005 | Schraga | 606/181 |
| 2006/0079920 A1 | 4/2006 | Schraga | |
| 2006/0100655 A1 | 5/2006 | Leong et al. | |
| 2006/0100656 A1 | 5/2006 | Olson et al. | |
| 2006/0106411 A1 | 5/2006 | Schraga | |
| 2006/0155317 A1 | 7/2006 | List | |
| 2006/0157362 A1 | 7/2006 | Schraga | |
| 2006/0173478 A1 | 8/2006 | Schraga | |
| 2006/0224172 A1 | 10/2006 | LeVaughn et al. | |
| 2006/0241668 A1 | 10/2006 | Schraga | |
| 2006/0247671 A1 | 11/2006 | LeVaughn | |
| 2006/0264996 A1 | 11/2006 | LeVaughn et al. | |
| 2006/0271084 A1 | 11/2006 | Schraga | |
| 2007/0055298 A1 | 3/2007 | Uehata et al. | |
| 2007/0083222 A1 | 4/2007 | Schraga | |
| 2007/0100364 A1 | 5/2007 | Sansom | |
| 2007/0173874 A1 | 7/2007 | Uschold et al. | |
| 2007/0173875 A1 | 7/2007 | Uschold | |
| 2007/0288047 A1 | 12/2007 | Thoes et al. | |
| 2008/0021493 A1 | 1/2008 | LeVaughn et al. | |
| 2008/0027474 A1 | 1/2008 | Curry et al. | |
| 2008/0033468 A1 | 2/2008 | Lathrop et al. | |
| 2008/0045992 A1 | 2/2008 | Schraga | |
| 2008/0058631 A1 | 3/2008 | Draudt et al. | |
| 2008/0065132 A1 | 3/2008 | Trissel et al. | |
| 2008/0077167 A1 | 3/2008 | Flynn et al. | |
| 2008/0082116 A1 | 4/2008 | Lathrop et al. | |
| 2008/0082117 A1 | 4/2008 | Ruf | |
| 2008/0146966 A1 | 6/2008 | LeVaughn et al. | |
| 2008/0147108 A1 | 6/2008 | Kennedy | |
| 2008/0195132 A1 | 8/2008 | Schraga | |
| 2008/0243159 A1 | 10/2008 | Schraga | |
| 2008/0255598 A1 | 10/2008 | LeVaughn et al. | |
| 2009/0030441 A1 | 1/2009 | Kudrna et al. | |
| 2010/0160942 A1 | 6/2010 | Lamps et al. | |
| 2010/0305501 A1* | 12/2010 | Ratjen | 604/82 |

OTHER PUBLICATIONS

International Search Report and Written Opinion for PCT/US2009/068674; Jun. 9, 2010; 18 pgs.

Invitation to Pay Additional Fees and Partial Search Report for PCT/US2009/068671; Apr. 8, 2010; 8 pgs.

International Search Report and Written Opinion for PCT/US2009/068671; Jun. 9, 2010; 18 pgs.

* cited by examiner

LANCING DEVICE AND LANCET

CROSS-REFERENCE TO RELATED APPLICATION

This application claims the benefit of U.S. Provisional Patent Application Ser. No. 61/138,768, filed Dec. 18, 2008, the entirety of which is hereby incorporated herein by reference for all purposes.

TECHNICAL FIELD

The present invention relates generally to the field of medical devices, and more particularly to lancets and lancing devices for blood sampling and testing.

BACKGROUND OF THE INVENTION

Lancets and lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. A lancet is typically propelled by the drive mechanism from a retracted position within the housing to an extended position wherein a sharp tip portion of the lancet projects from the housing to prick the subject's skin at a desired lancing site. A depth-control mechanism can optionally be provided to adjust the penetration depth of the lancet.

The lancet is typically a disposable component that is removably mounted into a receiver or lancet carrier portion of the drive mechanism of a lancing device. A used lancet typically is removed from the lancet carrier after sampling for disposal. An ejection mechanism can optionally be included for discharge of the used lancet from the lancing device. A new, sterile lancet is then replaced into the lancet carrier for further sampling. Lancets typically comprise a sharp metal tip in the form of a needle or blade. The needle or blade is typically embedded in a plastic body that has a size and shape configured for releasable engagement with the receiver or lancet carrier of a lancing device. The sharp tip of the lancet is commonly embedded in a removable plastic cap to maintain sterility and prevent inadvertent sticks prior to use. The end-cap may be replaceable onto the lancet after use to re-cover the sharp lancet tip for safety and hygienic purposes.

It is to the provision of improved lancing devices and lancets that the present invention is primarily directed.

SUMMARY OF THE INVENTION

In example embodiments, the present invention provides an improved lancing device, an improved lancet, and a system including a lancing device with a proprietary or device-specific lancet. Example embodiments include an improved depth-adjust mechanism for selectively varying the penetration depth of the lancet, an improved lancet ejector system using a protrusion or surface of the lancet to eject a used lancet from the lancing device, and/or an improved guidance system for guiding the path of travel of the lancet along its lancing stroke.

In one aspect, the invention relates to a lancing device including a housing, a lancet carrier mounted within the housing for movement between a retracted position and a lancing position, and a depth-control mechanism. The depth-control mechanism includes a dial rotationally mounted relative to the housing, and a linkage coupled to the dial and having a contact face for limiting travel of the lancet carrier at the lancing position.

In another aspect, the invention relates to a lancing system including a lancet and a lancing device for receiving and discharging said lancet. The lancet includes a lancet body having a proximal end and a distal end, and a sharp lancing tip projecting axially from the proximal end of the lancet body. The lancing device includes an ejector arm having an ejection actuator at a first end thereof and an abutment finger projecting from the ejector arm for abutment against the distal end of the lancet upon operation of the ejection actuator.

In still another aspect, the invention relates to a lancing device including an outer housing, a lancet carrier translationally movable within the housing, and an inner guidance housing mounted within the outer housing for constraining the lancet carrier to axial movement along a linear lancing stroke.

In another aspect, the invention relates to a lancing device including a lancet carrier comprising a lancet carrier stop, a drive spring for propelling the lancet carrier along a lancing stroke defining a stroke distance, and a depth control mechanism. The depth control mechanism includes a dial that is rotational about a center of rotation, the dial further comprising a mounting pin eccentrically offset from the center of rotation; and a stop bar having a first end mounted to the mounting pin of the dial and a second end comprising a stop surface for contact with the lancet carrier stop to adjust the stroke distance of the lancet carrier.

In another aspect of the invention, a lancing system includes a lancet and a lancing device for receiving and discharging the lancet. The lancet includes a lancet body having a contact surface, for example at a distal end of the lancet body, and a sharp lancing tip projecting axially from a proximal end of the lancet body. The lancing device includes an ejection mechanism comprising an abutment finger or fin projecting from an ejector arm for contacting the contact surface of the lancet, releasing the lancet from the lancet carrier or receiver, and ejecting the lancet from the lancing device.

In still another aspect of the invention, a lancet includes a lancet body, a sharp lancing tip projecting axially from a proximal end of the lancet body, and a flared flange projecting transversely from the lancet body.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
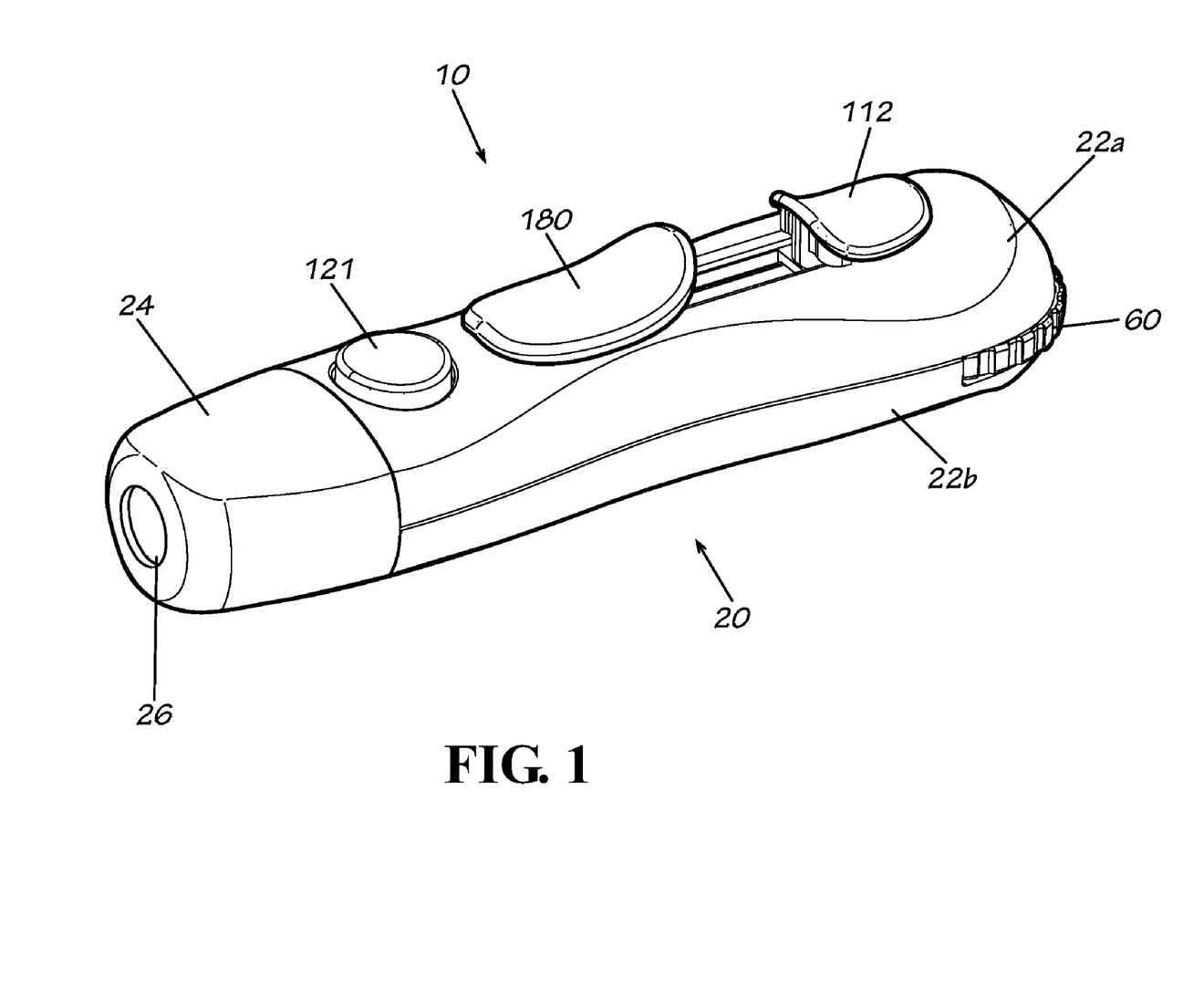
FIG. 1 is a perspective view of a lancing system including a lancing device and a lancet according to an example embodiment of the present invention.

With reference now to the drawing figures, wherein like reference numbers represent corresponding parts throughout the several views, FIG. 1 shows a lancing device 10 and lancet 12 according to example forms of the invention. The lancet 12 is optionally configured in size and shape to be specific or proprietary to the lancing device of the invention, whereby the lancing device and lancet comprise a complementary system. While the lancing device and lancet can take a variety of forms, in the depicted embodiments the lancing device comprises a housing 20 formed of upper and lower half-shells 22a, 22b, and optionally a removable proximal endcap 24 with a contact face having a lancet opening 26 therein for allowing passage of the sharp lancet tip during lancing.

FIGS. 2-6 show internal components of the lancing device 10 with the outer housing removed. The lancing device 10 comprises a drive mechanism comprising a lancet carrier 30, a drive spring 40 for propelling the lancet carrier from a retracted position within the housing to an extended or lancing position with the sharp lancet tip projecting out of the housing, and a return spring 42 for returning the lancet carrier to a neutral position within the housing after use. The lancing device further comprises a charging mechanism for retracting the lancet carrier from the neutral position to the retracted position and compressing the drive spring; and an activation mechanism for releasing the lancet carrier from the retracted position to traverse the lancing stroke from the retracted position, through the lancing position, and back to the neutral position. The lancing device optionally further comprises one or more of a depth-control mechanism, an ejector mechanism, and/or a guidance mechanism, and/or any combination thereof. These mechanisms or subsystems will be described in greater detail below.

Depth-Control Mechanism

Figure 3:
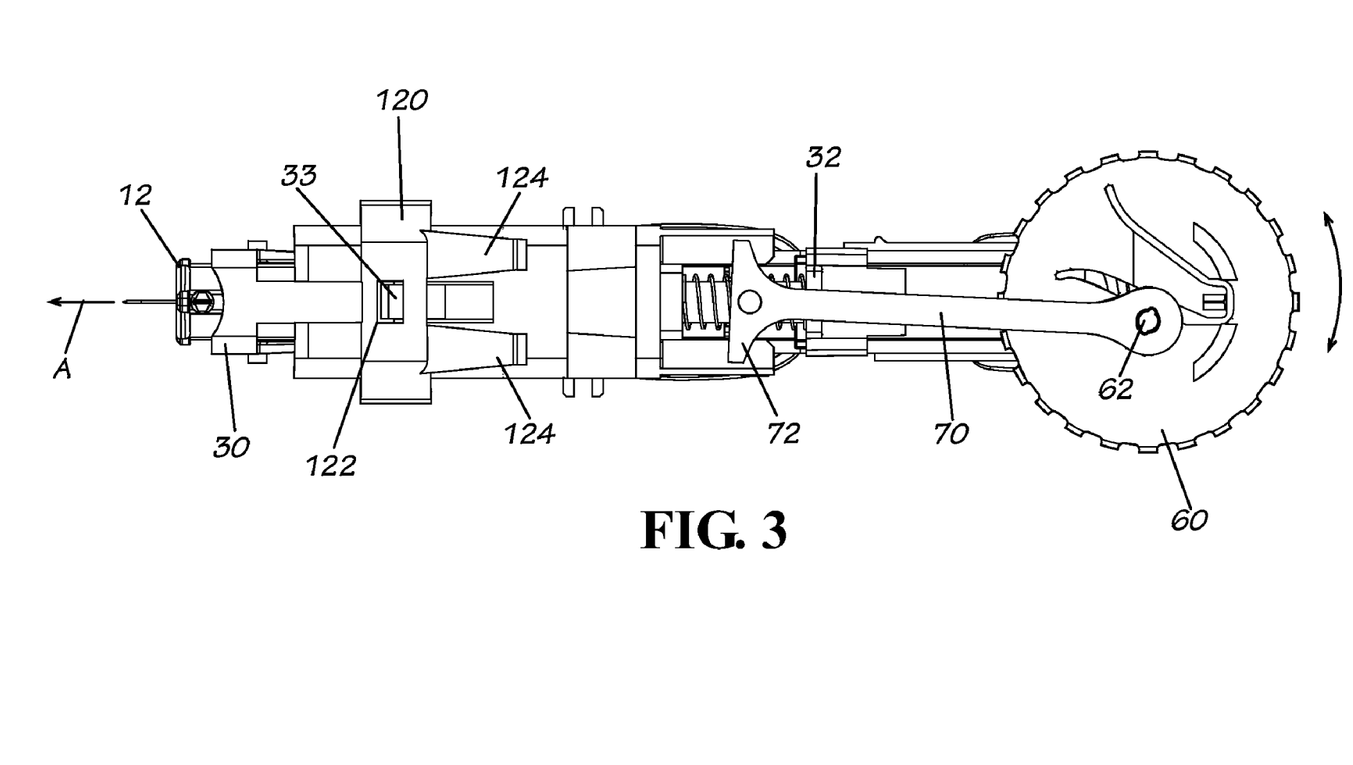
FIG. 3 is a bottom view of the internal mechanism of the lancing device of FIG. 1.
Figure 4A:
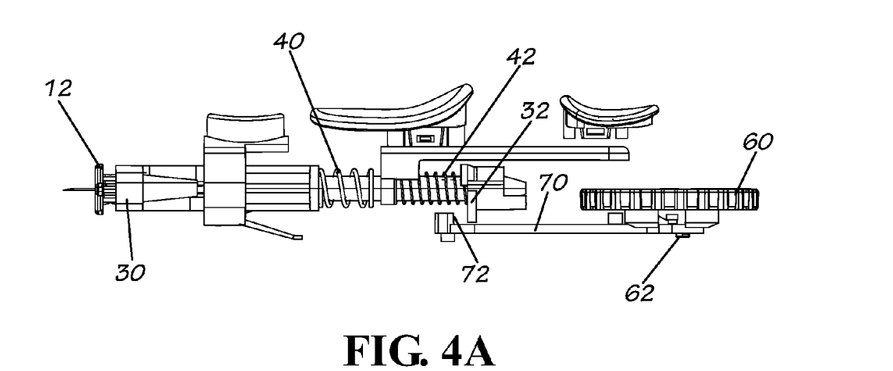
FIGS. 4A, 4B and 4C show a sequence of adjustment of a depth-control mechanism subsystem of the lancing device of FIG. 1.
Figure 4B:
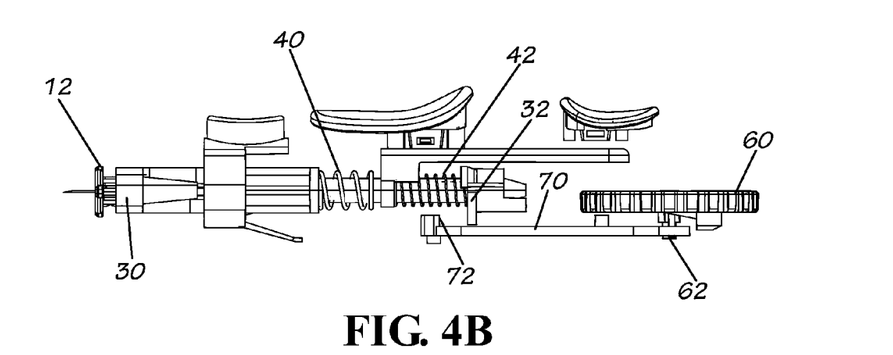
Figure 4C:
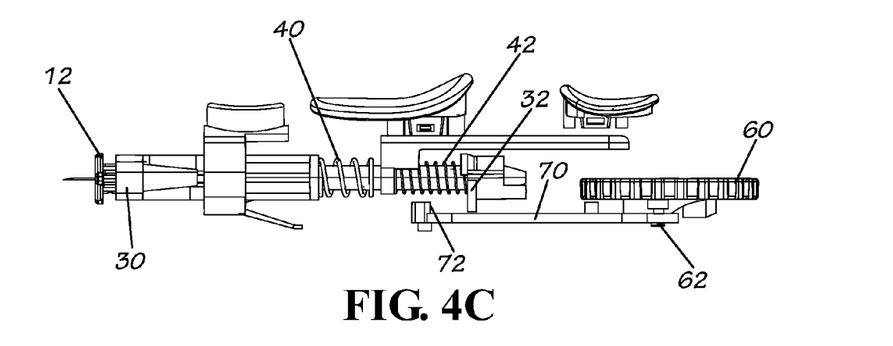

The depth of puncture provided by the lancing device can be adjusted so that the lancing process generates a sample of the necessary amount of blood for a successful blood glucose reading or other procedure while reducing, minimizing or eliminating undue pain to the subject. FIGS. 3 and 4 show an example depth-control mechanism according to the present invention. The depth-control mechanism comprises a depth-adjust dial 60 having a manipulation surface that the patient rotates to easily change the depth of puncture. In example forms, the dial rotates in a horizontal plane along the medial axis of the device housing, mounted between the upper and lower half-shells 22a, 22b. In alternate embodiments, the orientation and location of the depth-adjust dial can vary. The depth-control mechanism further comprises a stop member directly or indirectly coupled to the dial, which acts as a limit of travel for the drive mechanism of the lancing device. In the depicted embodiment, the dial is mounted at the distal or rearward end of the housing and rotates about an axis of rotation that is generally perpendicular to the path of travel of the lancet along its lancing stroke. The stop member acts on a transverse protrusion or other surface of the lancet holder or on a protrusion attached to the lancet holder as the lancet holder moves through its lancing stroke, to arrest the forward motion of the lancet holder and limit the travel of the lancet thereby defining the proximal or forward extent of travel of the lancet tip in its fully extended position. By turning the dial 60, the axial position of the stop member is changed thereby adjusting the point of contact of the lancet holder with the stop member relative to the outer housing, and in this manner the depth of penetration of the lancet is adjusted.

In example embodiments, the depth dial 60 is partially shielded within the device housing to improve the safety and user comfort delivered by the device by avoiding or reducing the incidence of unintentional depth adjustment that could cause unnecessary penetration depth. The rear end of the housing optionally is radiused to generally match the profile of the dial 60 with only the outer periphery of the dial projecting beyond the rearward end of the housing. The dial 60 preferably comprises numerical or other indicia visible on a portion of the dial from external of the rear end of the housing or through an opening or cutout portion of the housing 20 proximal its rear end, indicating the depth setting to the user. The mechanism of the depth dial preferably provides a smooth transition between depth settings and a clear indication of the depth setting, for example through a cutout on the housing 20. A resilient finger or segment of the dial 60 interacts with detents or other indexing features of the housing to provide tactile feedback to the user of the depth settings, and to retain the depth-adjust mechanism in a set position. The dial 60 optionally has a scalloped, stepped, ridged or knurled edge for ease of adjustment.

In the depicted embodiment, the depth-control mechanism comprises an arm or other linkage 70 comprising the contact face or stop 72 at its proximal end for limiting the stroke of travel of the lancet carrier 30. The linkage 70 is coupled at its distal end to an eccentric pin 62 projecting from the depth-adjust dial 60, so that rotation of the dial causes translation of the linkage 70 in the axial direction, and thereby adjusts the linear positioning of the stop 72. A larger diameter dial 60 with a smaller eccentric offset of the pin 62 from the center or axis of rotation of the dial can be used to adjust the depth in small increments with larger rotational increments of the dial for ease of use by users with reduced manual dexterity. Optionally, the dial moves through one or more indexed positional settings or through a continuous adjustment range, allowing the user to have an improved tactile feel between depth settings. Provision of a linkage 70 between the dial and the stop, and/or a stop member 72 formed for example of a substantially rigid but resilient material optionally acts as a vibration reducer, decreasing the transfer of energy or impact sensed by the user upon contact of the lancet carrier with the stop.

In example embodiments, the depth dial 60 rotates through a range of motion of at least about 45-90 degrees to about 270 degrees, for example about 180 degrees. An arcuate flange on the lower face of the dial 60 optionally rotates within a corresponding arcuate track or channel in the lower housing half shell 22b, or an axle extending from the dial rotates within a corresponding sleeve, bushing or bearing of the housing. The stop bar 70 is optionally generally T-shaped in profile, having a transversely extending rib forming the contact face 72 at its proximal end for limiting the stroke of the lancet carrier, and is connected at its distal end via a receiver opening or yoke 74 to the eccentric pin of the dial. The stop bar 70 optionally includes guidance features which engage the lancing device housing or other fixed part of the lancing device and allow the stop bar to translate in only one axis but to rotate freely around an axis parallel to the axis of rotation of the depth dial. Rotation of the dial selectively varies the position of the contact face 72, thereby adjusting the depth of penetration of the lancet at the lancing site.

The lancet carrier 30 or other portion of the drive mechanism includes a contact element for abutment with the contact face 72 of the stop bar to limit the travel of the lancet carrier and thereby control the penetration depth. In the depicted embodiment, the lancet carrier 30 comprises a distal extension arm with an end having a contact element with a projection or finger 32 mounted thereon. The projection or finger 32 extends downwardly to contact the upwardly directed contact face 72 of the stop bar as the lancet carrier 30 traverses the forward portion of its lancing stroke. The contact element optionally takes the form of a sleeve held on the split distal end of the lancet carrier by one or more resilient barbs to retain the return spring 42 in place on the distal extension arm of the lancet carrier.

As the dial 60 is rotated, the axial distance that the stop bar 70 moves is determined by how far the eccentric pin 62 is offset from the center of rotation of the dial and the angle through which the dial is moved. Additionally, the distal end of the stop bar moves transversely due to rotation of the dial to which it is coupled causing pivotal movement of the stop bar. Thus, there are two components of the movement of the stop bar 70: an axial translational component along the long axis of the stop bar, and a transverse component perpendicular to the long axis of the stop bar. In the depicted embodiment, movement along the long axis of the stop bar 70 provides the majority of the depth adjustment. Specifically, for a dial rotation of 180 degrees, the bar 70 moves an axial distance about equal to twice the radial displacement or offset of the eccentric pin 62 from the center of rotation of the dial. For 90 degree rotation of the dial, the stop bar 70 moves (along the axis of interest) a distance about equal to the radial displacement or offset of the eccentric pin 62 from the center of rotation of the dial. The movement in the direction perpendicular to the long axis of the stop bar is converted to a pivotal toggling movement of the bar 70, which results in angular displacement of the stop surface 72. By varying the curvature of the stop surface 72 which contacts the contact surface of the lancet carrier, this angular movement can be utilized to fine-tune the stop position and thereby the depth setting.

Any number of angular positions of the dial can be converted into discrete movements of the stop bar through the addition of indexing detents acting on either the dial or the stop bar. Also, while the depicted embodiments show the depth stop acting on only one side of the lancet carrier or firing mechanism, the provision of a stop bar which can act on two or more sides of the lancet carrier or firing mechanism is within the scope of the invention. And while the depicted embodiments show a configuration for controlling depth by limiting the lancing stroke by contact with the back end of the lancet carrier or firing mechanism, the depth control mechanism of the present invention also includes embodiments that limit the lancing stroke by contact with any point of the lancet carrier or firing mechanism from the rear up to and including the front where the lancet is engaged.

Ejector Mechanism

FIGS. 2, 3, 5A and 5B show a lancet ejection mechanism 100 for removal of a lancet from the lancet carrier 30. The lancet 12 of the lancing system of the present invention is optionally a low-mass proprietary lancet. Because there is less mass being driven during the activation of the device, the lancet may be propelled in and out of the subject's skin faster and with less vibration. Although the present invention is not bound to or limited by theory, faster puncture with a lower mass lancet is believed to reduce pain levels experienced by the subject. But the low-mass lancet generally has a smaller surface area and therefore may be more difficult to handle. Because of the very small size of the lancet 12, a large endcap, or a collar or flange having an expanded or flared transverse dimension is optionally provided at the proximal end of the lancet body for easier manipulation and improved handling.

Figure 5A:
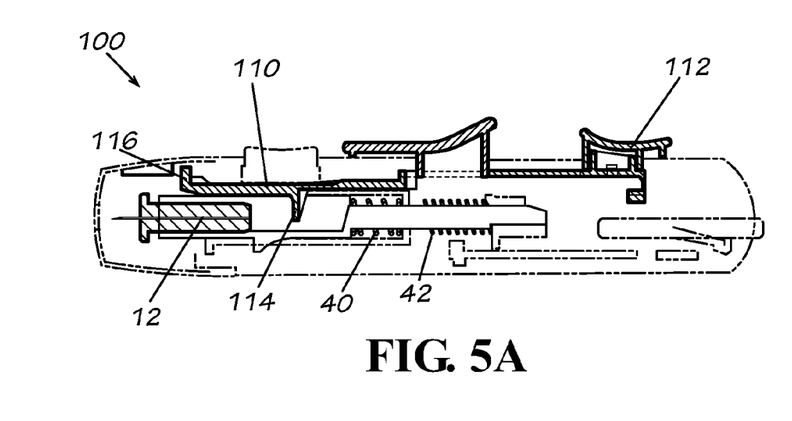
FIGS. 5A and 5B show a sequence of operation of a lancet-ejection subsystem of the lancing device of FIG. 1.
Figure 5B:
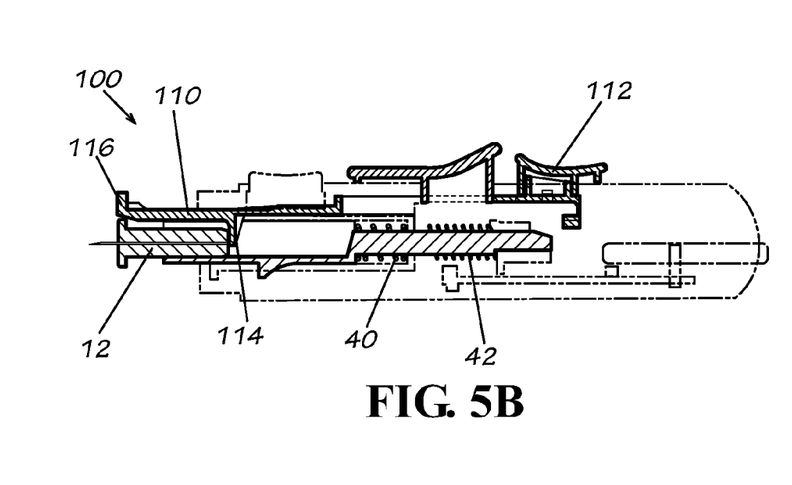

The ejection mechanism 100 of the depicted embodiments comprises an ejector arm 110 slidably mounted between the lancet carrier 30 and a release button sleeve 120. The ejector arm 110 includes an ejection actuator 112 providing a user interface for the user to manually operate the mechanism, and an abutment finger 114 extending transversely from the ejector arm for contacting the rearward end or other contact surface of the lancet 12 to push the lancet out of engagement with the lancet carrier. A notch or opening 122 in the lower face of the release button sleeve 120 engages a cooperating catch or projection 33 of the lancet carrier 30 to limit the forward movement of the lancet carrier as the lancet is ejected, and leaf springs 124 or other biasing means bias the sleeve 120 upward and into engagement with the lancet carrier unless the release button is pressed downwardly to activate the lancing device. A protrusion 116 on the ejector arm interferes with a cooperating protrusion on the housing endcap to prevent operation of the ejection mechanism unless the endcap is removed.

Guidance Mechanism

Figure 2:
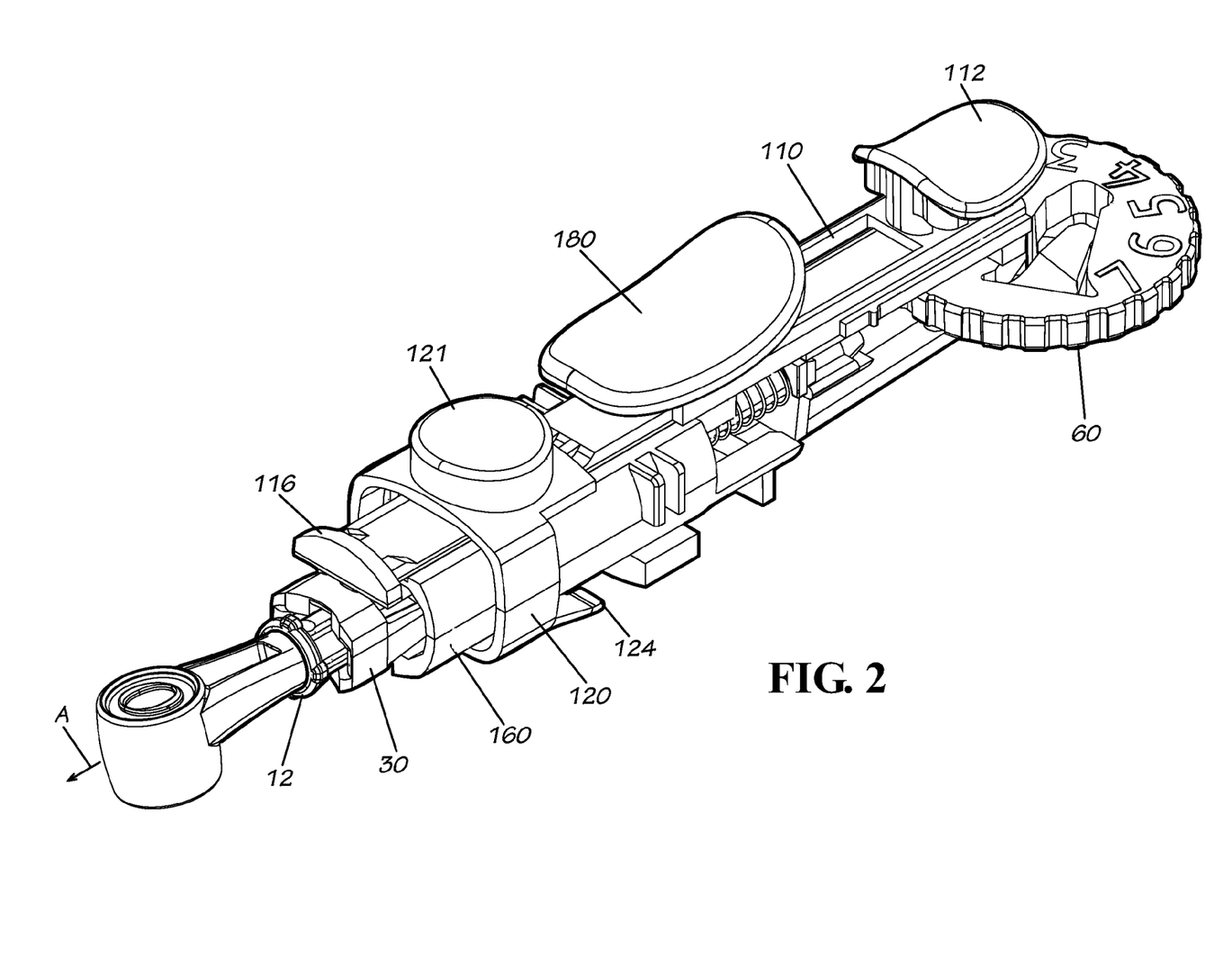
FIG. 2 is another perspective view of the lancing device of FIG. 1, with its outer housing removed to show internal components.
Figure 7A:
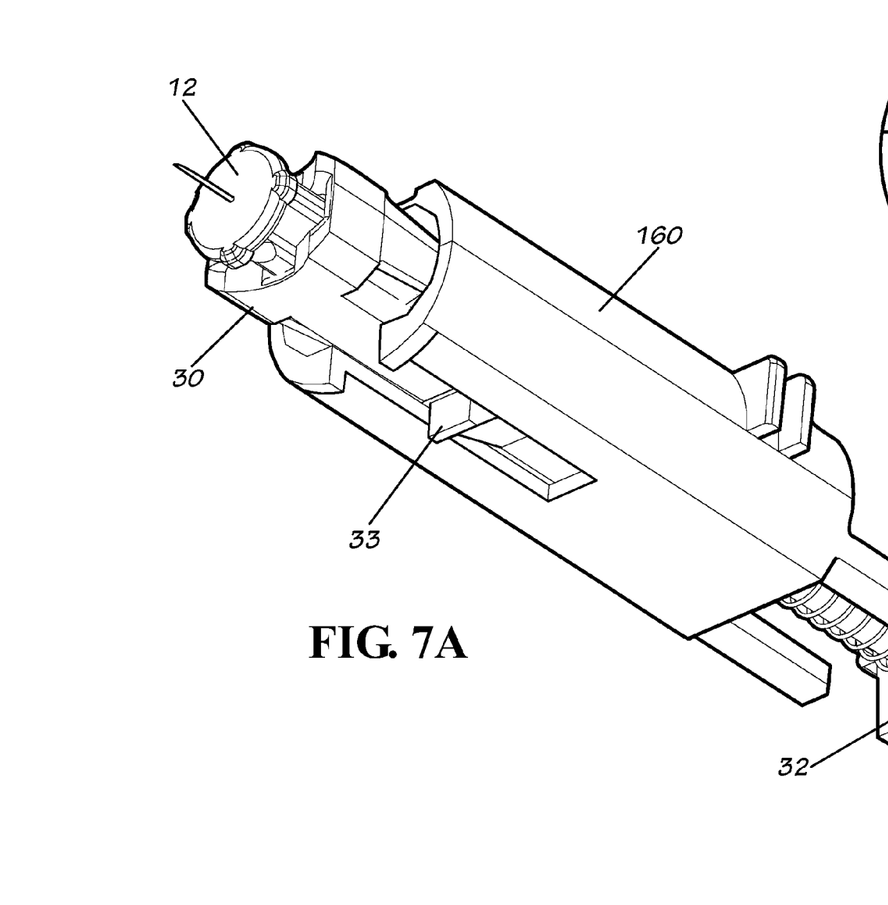
FIGS. 7A and 7B show lancet guidance components of the lancing device of FIG. 1.
Figure 7B:
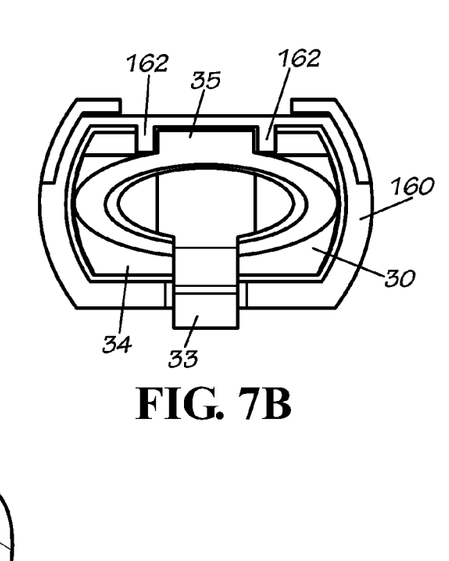

The guidance mechanism 150 of the present invention is shown in example form in FIGS. 2, 7A and 7B. While the present invention is not bound to or limited by theory, it is believed that in general, all else being equal, the smaller the side-to-side movement of the lancet needle (movement of the lancet tip transverse to the lengthwise axis of the lancet needle as it moves along the lancing stroke) during the lancing stroke and in particular as the lancet tip is penetrating the subject's skin at the lancing site, the lower the pain level experienced by the subject. Thus, the guidance mechanism of the present invention is configured to constrain the lancet to a relatively straight linear stroke or path of travel.

Minimizing the number of parts involved in the guidance mechanism advantageously reduces tolerance stacking and play between parts, making it easier to tightly control/limit the side-to-side movement of the lancet holder as it travels forward. Accordingly, the guidance mechanism 150 of the present invention consists of only a single fixed inner guidance housing 160 and a single moving member, namely the lancet carrier 30. The inner guidance member 160 generally comprises a hollow sleeve having an internal channel with a shape and dimensions configured to generally match one or more outer surfaces or profile elements of the lancet carrier 30, and thereby allow freely sliding movement of the lancet carrier along the lancing axis A, but minimize out-of-axis movement in any direction.

In example forms, the inner guidance housing 160 comprises a slot defined between a pair of spaced vertical struts 162, and the lancet carrier 30 comprises an elongate rib 35 having a profile matching the slot with a close running fit. Additionally or alternatively, the lancet carrier 30 comprises a flange 34 having an outer profile generally matching the inner profile of the channel of the inner guidance housing 160 with a close running fit. The inner guidance housing 160 and/or one or more components affixed thereto is/are engaged within the outer housing 20 at one or more points of contact to prevent relative play therebetween. In this manner, the inner guidance housing 160 and the drive mechanism constitute a drive chassis that can be mated to different outer housing configurations.

Charging and Activation

Figure 6A:
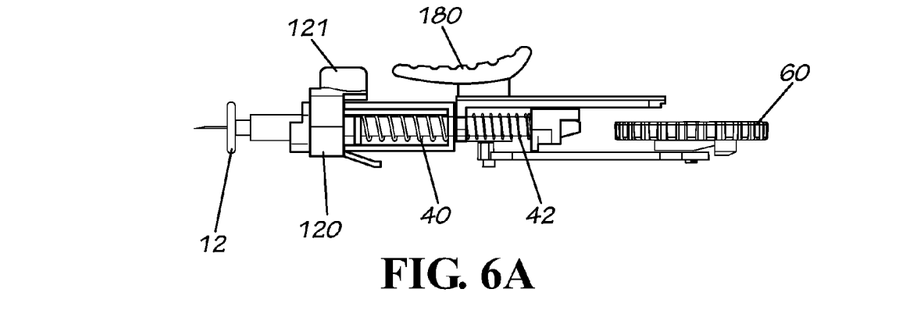
FIGS. 6A, 6B and 6C show a sequence of operation of the lancing device of FIG. 1, in its rest, charging and firing positions, respectively.
Figure 6B:
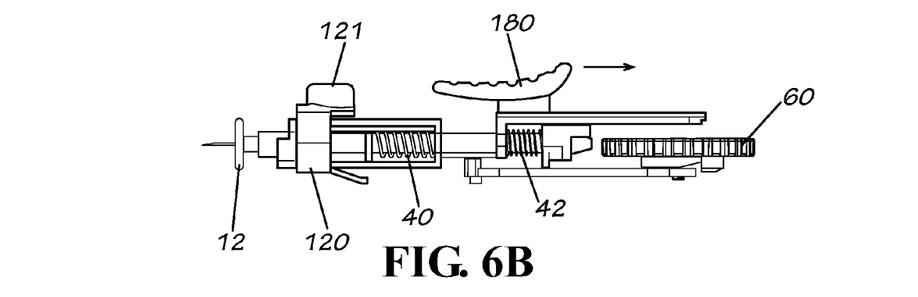
Figure 6C:
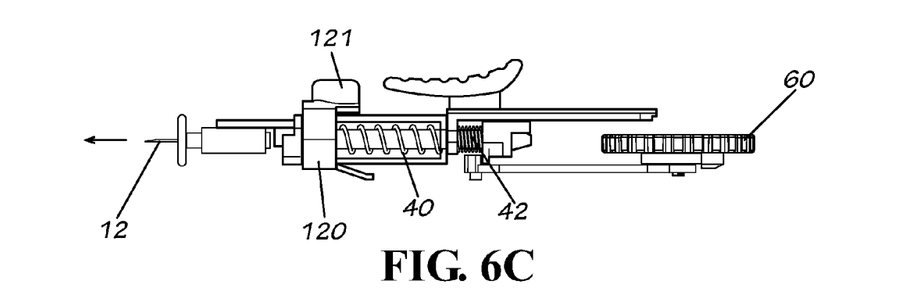

FIGS. 6A, 6B and 6C show a sequence of operation and method of use of the lancing system according to an example form of the invention. FIG. 6A shows the inner mechanism of the lancing device 10 in a rest or neutral position. The drive spring 40 and return spring 42 are uncompressed (or relatively uncompressed) and in equilibrium. The catch 33 of the lancet carrier is engaged in the opening 122 in the lower face of the release button sleeve 120 to prevent the lancet carrier from moving substantially forward when a lancet is ejected or installed into the receiver of the lancet carrier.

FIG. 6B shows the lancing device in a charging position. The user slides the charging actuator 180 rearward, compressing the drive spring 40 between a retention flange on the lancet carrier and the guidance housing. The inclined rear face of the catch 33 of the lancet carrier 30 presses the release button 121 and release button sleeve 120 downward against the bias of leaf springs 124. As the forward catch surface of the catch 33 clears the rear edge of the release button sleeve 120, the leaf springs pop the sleeve and release button back up to retain the lancet carrier 30 in the charged or cocked position.

FIG. 6C shows the lancing device in a firing or activated position. The user places the lancet opening 26 of the endcap against the skin at the intended lancing site and presses the release button 121, which moves the release button sleeve 120 downward against the bias of the leaf springs 124, releasing the catch 33 of the lancet carrier from the release button sleeve and allows the drive spring to extend and propel the lancet carrier and lancet forward through the lancing stroke to penetrate the subject's skin at the lancing site. The return spring 42 then retracts the lancet tip to a shielded position back within the housing, returning to the rest or neutral state.

Lancet

Figure 8A:
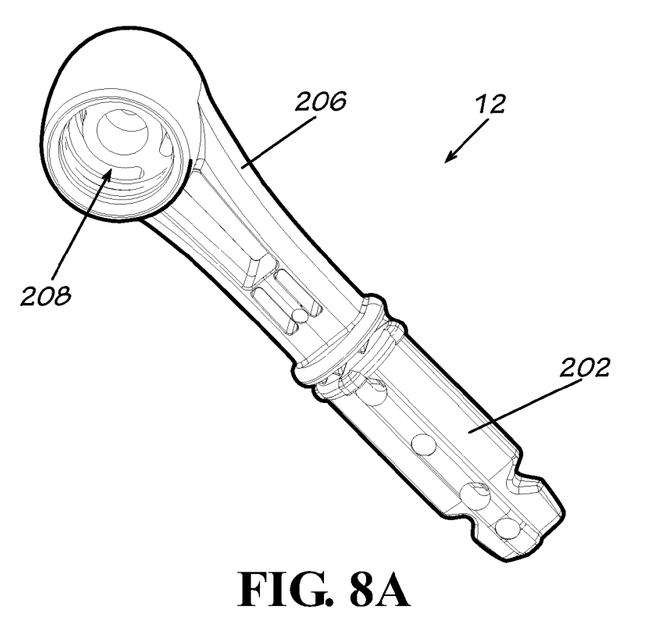
FIGS. 8A, 8B and 8C show a lancet according to an example embodiment of the present invention, in its intact, cap-removed and disposal states, respectively.
Figure 8B:
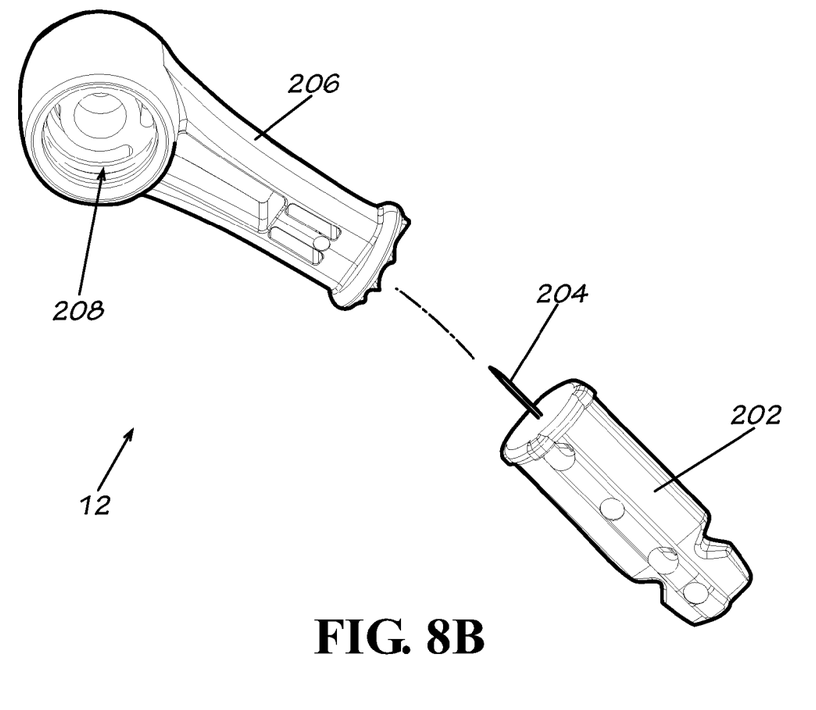
Figure 8C:
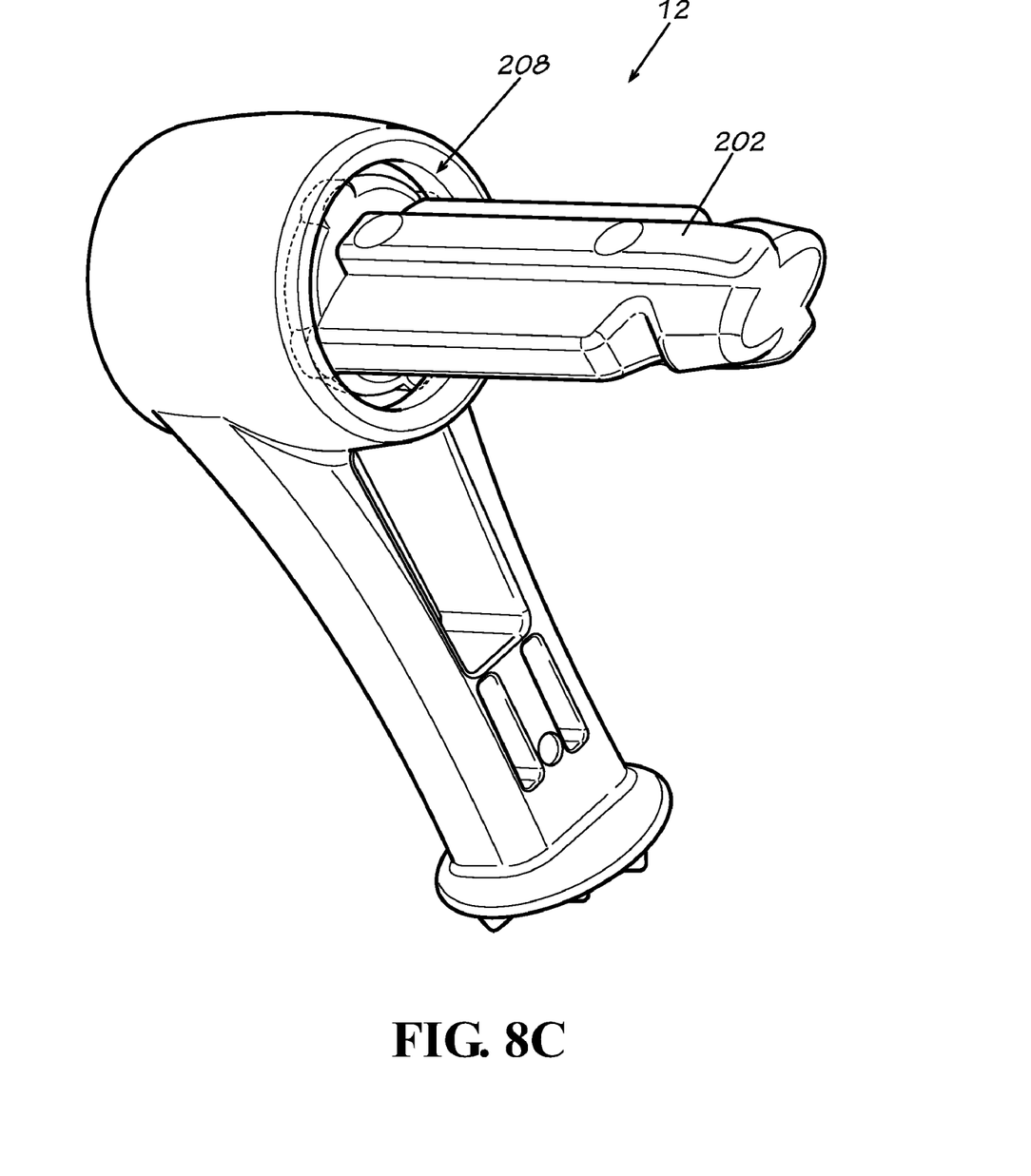

FIGS. 8A, 8B and 8C show a lancet 12 according to an example form of the invention. The lancet includes a lancet body 202, a sharp lancet needle or blade 204 having a tip projecting from a proximal end of the lancet body, and a detachable endcap 206 having a distal end initially attached to the proximal end of the lancet body and having the tip of the lancet embedded therein as shown in FIG. 8A. The endcap 206 is detachable from the lancet body 202 as shown in FIG. 8B to expose the sharp lancet tip. After use, the sharp tip may be inserted into the shroud 208 at the proximal end of the endcap to prevent inadvertent needle-sticks. Optionally, the lancet body 202 is configured to be proprietary or device-specific, wherein only a specified lancet design will engage within a particular lancing device type. Alternatively the body may be of standard or universal format.

While the invention has been described with reference to preferred and example embodiments, it will be understood by those skilled in the art that a variety of modifications, additions and deletions are within the scope of the invention, as defined by the following claims.

What is claimed is:

1. A lancing device comprising a housing, a lancet carrier mounted within said housing for movement between a retracted position and a lancing position, and a depth-control mechanism, said depth-control mechanism comprising a dial rotationally mounted relative to said housing, and a linkage coupled to said dial and having a stop member for limiting travel of the lancet carrier at the lancing position, wherein rotation of the dial causes movement of the linkage to adjust a point of contact of the lancet carrier with the stop member relative to the housing, and wherein the linkage comprises a stop bar having a generally T-shaped profile with a lengthwise axis and a traverse rib forming the stop member and extending generally perpendicular to the lengthwise axis.

2. The lancing device of claim 1, wherein said linkage comprising the stop bar has a first end coupled to an eccentric pin of the dial and a second end comprising the stop member.

3. The lancing device of claim 1, wherein rotation of the dial drives translational movement of the stop member to adjust a point of contact of the lancet carrier with the stop member relative to the housing to vary a penetration depth of the lancing device.

4. The lancing device of claim 3, wherein rotation of the dial also drives pivotal movement of the stop member.

5. The lancing device of claim 1, wherein the dial is mounted at a distal end of the housing opposite a lancet opening.

6. The lancing device of claim 5, wherein the distal end of said housing comprises a cutout portion, and wherein the dial comprises indicia viewable in the cutout portion and indicating a lancing depth setting corresponding to a rotational position of the dial.

7. The lancing device of claim 1, wherein the stop member limits travel of the lancet carrier at the lancing position by direct contact between the stop member and the lancet carrier.

8. The lancing device of claim 1, wherein the stop member limits travel of the lancet carrier at the lancing position by indirect contact between the stop member and a component mounted to the lancet carrier.

9. The lancing device of claim 1, further comprising a drive spring for driving the lancet carrier along at least an advancement portion of a lancing stroke.

10. The lancing device of claim 9, further comprising a return spring for driving the lancet carrier along a return portion of a lancing stroke.

11. The lancing device of claim 1, wherein the lancet carrier traverses a lancing stroke in an axial direction, and wherein the dial rotates about an axis of rotation generally perpendicular to the axial direction.

12. The lancing device of claim 11, wherein the dial rotates in a plane along a medial axis of the housing.

13. The lancing device of claim 1, wherein rotation of the dial drives an axial component of motion of the stop bar and a transverse component of motion of the stop bar.

14. The lancing device of claim 13, wherein the axial and transverse components of motion generate a pivotal motion of the stop bar.

15. The lancing device of claim 1, wherein a rearward end of the housing is radiused to generally match a profile of the dial.

16. The lancing device of claim 15, wherein only an outer periphery of the dial projects beyond the rearward end of the housing.

17. A lancing device comprising a housing, a lancet carrier mounted within said housing for movement in an axial direction between a retracted position and a lancing position, at least one spring for driving the movement of the lancet carrier, and a depth-control mechanism, said depth-control mechanism comprising a dial rotational about an axis generally transverse to the axial direction, and a linkage coupled to said dial and having a stop member for limiting travel of the lancet carrier at the lancing position, wherein rotation of the dial causes movement of the linkage to adjust a point of contact of the lancet carrier with the stop member relative to the housing, and wherein the linkage comprises a stop bar having a generally T-shaped profile with a lengthwise axis and a traverse rib forming the stop member and extending generally perpendicular to the lengthwise axis.

18. The lancing device of claim 17, wherein rotation of the dial drives an axial component of motion of the stop bar and a transverse component of motion of the stop bar.

19. The lancing device of claim 18, wherein the axial and transverse components of motion generate a pivotal motion of the stop bar.

20. The lancing device of claim 17, wherein the dial rotates in a plane along a medial axis of the housing.

21. The lancing device of claim 17, wherein a rearward end of the housing is radiused to generally match a profile of the dial.

22. The lancing device of claim 21, wherein only an outer periphery of the dial projects beyond the rearward end of the housing.

* * * * *